United States Patent [19]

Nishio

[11] Patent Number: 4,910,995

[45] Date of Patent: Mar. 27, 1990

[54] DROP TESTER CAPABLE OF AUTOMATICALLY AND REPEATEDLY CARRYING OUT A DROP TEST

[75] Inventor: Yasuyuki Nishio, Yamanashi, Japan

[73] Assignee: Hoya Corporation, Tokyo, Japan

[21] Appl. No.: 330,145

[22] Filed: Mar. 29, 1989

[30] Foreign Application Priority Data

Mar. 31, 1988 [JP] Japan .................................. 63-79835

[51] Int. Cl.[4] .............................................. G01N 3/34

[52] U.S. Cl. ........................................................ 73/12

[58] Field of Search ............................................. 73/12

[56] References Cited

U.S. PATENT DOCUMENTS 2,159,036 5/1939 McSwain ................................ 73/12

*Primary Examiner*—Charles A. Ruehl

*Attorney, Agent, or Firm*—Ladas & Parry

[57] ABSTRACT

In a drop tester for repeatedly dropping an article from a predetermined height, the article is vertically suspended by a string which is guided through a guide member to a fixed support post. The string is reciprocally pulled by a drive member on a side of the fixed support post to hoist the article to the predetermined height and is thereafter released to drop the article. A detection member is located at the predetermined height to produce a detection signal when the article reaches the predetermined height. The drive member horizontally pulls the string within a predetermined distance with the string brought into contact with a retractable drive pin. The drive pin is retracted when the detection signal is produced by the member to release the string from the drive pin and to thereby drop the article.

8 Claims, 6 Drawing Sheets

DROP TESTER CAPABLE OF AUTOMATICALLY AND REPEATEDLY CARRYING OUT A DROP TEST

BACKGROUND OF THE INVENTION

This invention relates to a drop tester for use in freely and repeatedly dropping a specimen or an article, such as a compact disk, a memory disk, a video disk, or the like.

In general, an article of the type described comprises a plastic plate, a glass plate, or the like and a thin film or films deposited thereon. In such an article, durability must be tested against a mechanical shock. For this purpose, the article should be subjected to a dropping test. At any rate, the dropping test is helpful to assure quality of the article by testing the durability against the mechanical shock.

A conventional dropping test has been made by freely and repeatedly dropping an article from a predetermined height to an object, such as a floor, again and again to give a mechanical shock to the article and by counting repetitions of dropping the article until the article is broken or destructed.

More specifically, the article is first located on a support member, such as a desk, having the predetermined height and is manually dropped towards a floor by an operator from the desk or the like. Thereafter, the article should be manually picked up by the operator to be located on the desk again. Such a very simple operation should be repeated by the operator again and again until the article is broken. Practically, such an operation must be carried out hundreds or thousands of times. Therefore, the conventional dropping test is terribly time-consuming and laborious.

SUMMARY OF THE INVENTION

It is an object of this invention to provide a drop tester which is capable of saving time and labor for a drop test.

It is another object of this invention to provide a drop tester of the type described, which is simple in structure.

It is still another object of this invention to provide a drop tester of the type described, which can automatically carrying out the drop test.

According to this invention, a drop tester is for use in freely and repeatedly dropping an article from a predetermined height to test durability of the article until the article is destructed. The drop tester comprises a string member having a first end for supporting the article, a second end, and an intermediate portion between the first and the second ends, guiding means for slidably guiding the string member to suspend the article, driving means associated with the string member at the second end through the guiding means for repeatedly and automatically driving the string member within a predetermined range to elevate the article to the predetermined height with the article held at the first end and to thereafter freely drop the article from the predetermined height, detecting means for detecting that the article is elevated to the predetermined height by the driving means to produce a detection signal each time when the article is elevated to the predetermined height and, otherwise, to stop producing the detection signal, counting means coupled to the sensing means for successively counting the detection signal until the detection signal is stopped to produce a count signal representative of a result of the count to display the accumulation signal, and display means coupled to the counting means for displaying the count signal.

DESCRIPTION OF THE PREFERRED EMBODIMENTS

Figure 1:
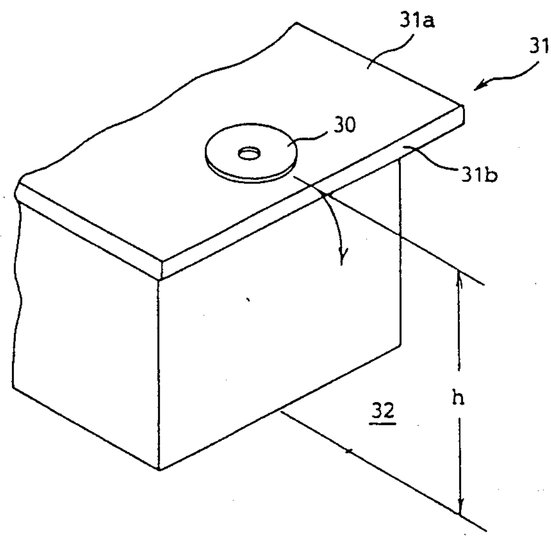
FIG. 1 is a view for use in describing a conventional drop test.

Referring to FIG. 1, description will be made as regards a conventional drop test for a better understanding of this invention. In FIG. 1, a compact disk 30 is exemplified as an article to be tested by the drop test. A desk 31 is disposed on a floor 32 and has a flat surface 31*a*, a side surface 31*b* contiguous to the flat surface 31*a* through an edge between the flat surface 31*a* and the side surface 31*b*, and a predetermined height h. On the drop test, the compact disk 30 is located on the flat surface 31*a* of the des 31 and is manually slidably moved towards the edge by an operator (not shown) on the flat surface 31*a*. As a result, the compact disk 30 is freely dropped from the edge towards the floor 32.

Figure 2:
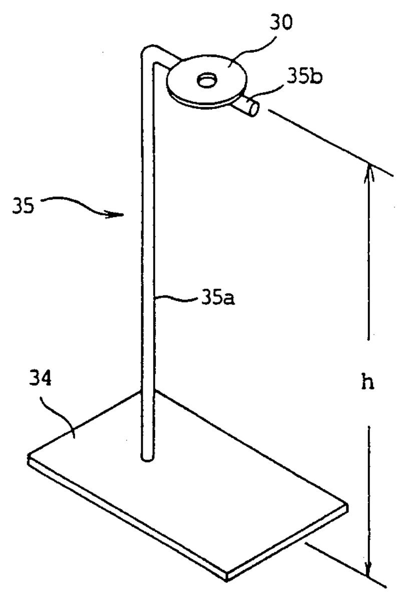
FIG. 2 is a view for use in describing another conventional drop test.

Referring to FIG. 2, another conventional drop test is made by the use of a stand 34 and a support member 35 of a rod shape fixed to the stand 34. The support member 35 has an upright portion 35*a* standing on the stand 34 and a bar portion 35*b* substantially perpendicular to the upright portion 35*a*. The bar portion 35*b* has a height h, like the desk 31 of FIG. 1, and serves as a support for the compact disk 30. On the drop test, the compact disk 30 is manually placed on the bar portion 35*b* by hand by an operator. Subsequently, the compact disk 30 is freely dropped when the operator releases the operator's hand from the compact disk 30.

Similar drop tests must be repeated until the article 30 is mechanically destructed. At any rate, the conventional drop tests are time-consuming and laborious because the compact disk 30 must be dropped again and again until breakage of the compact disk 30, as pointed out in the preamble of the instant specification.

Figure 3:
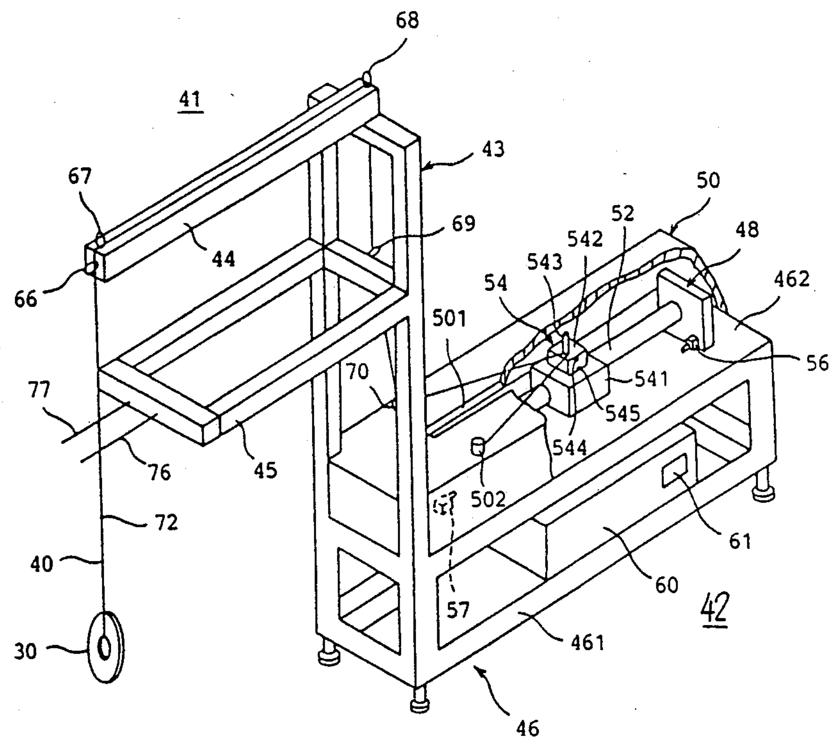
FIG. 3 shows a perspective view of a drop tester according to a first embodiment of this invention with a part cut away.

Referring to FIG. 3, a drop tester according to a first embodiment of this invention is assumed to be used for testing a compact disk 30, like in FIGS. 1 and 2. As shown in FIG. 3, the compact disk 30 is substantially vertically suspended by a string or thread 40 which may be, for example, a fishing line. In FIG. 3, the compact disk 30 is automatically elevated or hoisted upwards of FIG. 3 to a predetermined height h and is automatically dropped from the predetermined height h down to a floor (unnumbered). The illustrated drop tester can automatically repeat an up-and-down operation until breakage of the compact disk 30 and counts repetitions of the up-and-down operations to indicate or display a count or the repetitions of the up-and-down operations.

To this end, the illustrated drop tester is located on the floor and comprises a guide section 41 and a drive section 42 mechanically attached to the guide section 41. The guide section 41 comprises a tower frame 43 standing upright and a guide bar 44 horizontally extended from an upper end of the tower frame 43. The guide bar 44 has a first preselected length, a first guide end fixed to the tower frame 43, and a second guide end. A support frame 45 is substantially horizontally extended from a middle portion of the tower frame 43. Thus, the support frame 45 is juxtaposed with the guide bar 44 at the predetermined height. Both the guide bar 44 and the support frame 45 are extended from the tower frame 43 forwards of FIG. 3.

On the other hand, the drive section 42 comprises a frame member 46 fixed to a lower end of the tower frame 43 and extended relative to the tower frame 43 backwards of FIG. 3. The frame member 46 defines a bottom frame 461 substantially horizontally extended relative to the floor and an upper shelf 462 substantially parallel to the bottom frame 461. On the upper shelf 462, a drive member 48 is mounted to repetitively or reciprocally drive the string 40 backwardly and forwardly of FIG. 3 in a manner to be described later.

The drive member 48 is accommodated in a drive member case 50 of a rectangular shape which is attached to the upper shelf 462 and which envelops the drive member 48. A narrow slit 501 is cut on an upper surface of the drive member case 50 and is extended from an adjacent part of the towed frame 43 backwardly of FIG. 3. In addition, a support post 502 is fixed to the upper surface of the drive member case 50 in the vicinity of the tower frame 4. The illustrated string 40 has a first end tied to the compact disk 30 and a second end fastened to the support post 502 through the guide section 41 in a manner to be described later.

The drive member 48 comprises a cylinder rod 52 of a nonmagnetic material disposed along the slit 501 and a moving unit 54 slidable along the cylinder rod 52 within a predetermined distance. The cylinder rod 52 surrounds a hollow space therein and is coupled to an actuator (not shown) operable in response to an electric signal to supply an air to the hollow space of the cylinder rod 52. The predetermined distance is determined by first and second limit switches 56 and 57 which are disposed at both ends of the cylinder rod 52 along the cylinder rod 52 and which are pressed by the moving unit 54. The moving unit 54 comprises a cylinder block 541 movable forwards or backwards along the cylinder rod 52 by an air or the like and an additional cylinder 542 mounted on the cylinder block 541. The cylinder block 541 comprises an inner magnet (not shown) slidable by the air in the hollow space of the cylinder rod 52 and an outer magnet (not shown) placed outside of the cylinder rod 52 and movable together with the inner magnet. Such a cylinder block is known as a rodless cylinder and will not be described any longer.

The additional cylinder 542 is associated with an additional actuator which is operable independently of the above-mentioned actuator in response to a electric signal. The additional cylinder 542 is supplied from the additional actuator with an air.

A cylinder pin 543 is projected from the additional cylinder 542 and is movable upwards or downwards of FIG. 3 within a preselected vertical range in a manner to be described later. In order to define the preselected vertical range, third and fourth limit switches 544 and 545 are attached to the additional cylinder 542. In the example being illustrated, the third and the fourth limit switches 544 and 545 serve to determine uppermost and lowermost limits of the cylinder pin 543, respectively.

In FIG. 3, a controller 60 is placed on a lower shelf 461 to control the drive member 48. For this purpose, the controller 60 comprises a control circuit electrically connected to the first through fourth limit switches 56, 57, 544, and 545 and the actuators. The control circuit serves to successively count repetitions of the up-and-down operations and may be recognized as a counter circuit. Furthermore, a display unit 61 is included in the controller 60 to visually display the repetitions of the up-and-down operations.

Now, the string 40 is guided through first through fifth guide rings 66, 67, 68, 69, and 70 to the support post 502. The first through third guide rings 66 to 68 are fixed to an end portion, a leftmost edge, and a rightmost edge of the guide bar 44, as shown in FIG. 3, respectively, while the fourth and the fifth guide rings 69 and 70 are attached to the tower frame 43 and the drive member case 50, respectively. The fifth guide ring 70 faces the support post 502 across the slit 501. In this connection, the guide bar 44, the tower frame 43, the support post 502, and the first through fifth guide rings 66 to 70 may be collectively referred to as a guide member for guiding the string 40 to the support post 502.

A weight 72 is attached to the intermediate portion of the string 40 to give tension to the string 40 when the compact disk 30 is vertically suspended from the guide bar 44, as illustrated in FIG. 3.

In addition, the support frame 45 has a rectangular shape and is formed by a pair of side bars projected from the tower frame 43 and front and rear bars connected to the side bars. From the front bar of the support frame 45, first and second detection needles 76 and 77 are protruded with a prescribed spacing left therebetween so that the string 40 passes through the spacing between the first and the second detection needles 76 and 77, in no contact with the front bar of the support frame 45. In this connection, the support frame 45 has a second preselected length shorter than the first preselected length of the guide bar 44, as readily understood from FIG. 3. The first and the second detection needles 76 and 77 are situated at the predetermined height h like in FIGS. 1 and 2 and are mechanically connected to micro switches (not shown). The micro switches are housed in the front bar of the support frame 45 and electrically connected to the controller 60. With this structure, the compact disk 30 is brought into contact with the first and the second detection needles 76 and 77 each time when the compact disk 30 is hoisted to the predetermined height h. The first and the second detection needles 76 and 77 close the micro switches to supply the controller 60 with an electric signal as a detection signal each time when the compact disk 30 is contacted with the first and the second detection needles 76 and 77. Each detection signal is counted up or accumulated in the control circuit of the controller 60.

At any rate, the support frame 45 is helpful to support the first and the second detection needles 76 and 77. The support frame 45, the first and the second detection needles 76 and 77, an the micro switches may be collectively called a detecting member for detecting that the compact disk 30 is hoisted to the predetermined height.

In order to hoist or drop the compact disk 30 to or from the predetermined height h, the string 40 should be pulled and released. The drive member 48 is helpful to carry out the above-mentioned operation, as will presently become clear.

Figure 4:
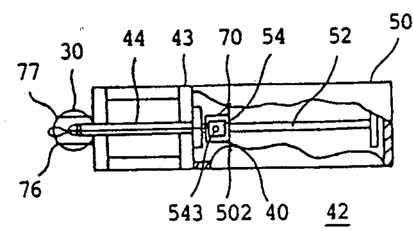
FIG. 4 shows, a plan view for use in describing an initial state of the drop tester illustrated in FIG. 3 with a part cut away.
Figure 5:
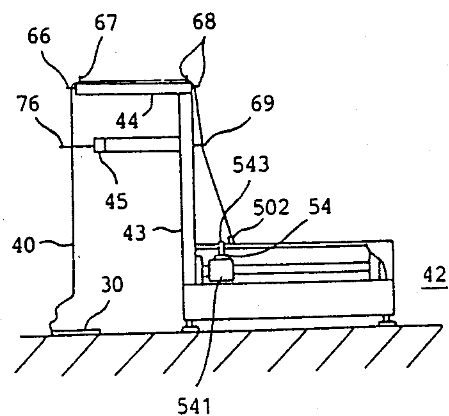
FIG. 5 shows an elevational view for describing the initial state of the drop tester illustrated in FIG. 3 with a part cut away.

Referring to FIGS. 4 and 5, the moving unit 54 is moved to a leftmost position along the slit 501 at an initial state. In this case, the cylinder pin 543 is retracted downwards, as shown in FIG. 5, and is located between the tower frame 43 and a portion of the string 40 adjacent to the support post 502 and the fifth guide rings 70, as shown in FIG. 4. In this event, the compact disk 30 is placed on the floor while the moving unit 54 is brought into contact with the second limit switch 57. As a result, the second limit switch 57 is closed to produce an electric signal. The electric signal is delivered to the controller 60 (FIG. 3) through an electrical connection line (not shown).

Figure 6:
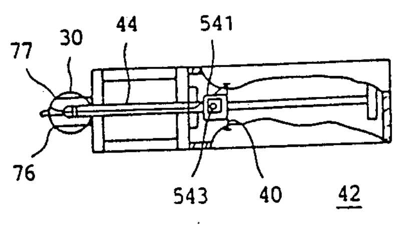
FIG. 6 shows a plan view for use in describing that state of the drop tester which follows the initial state.
Figure 7:
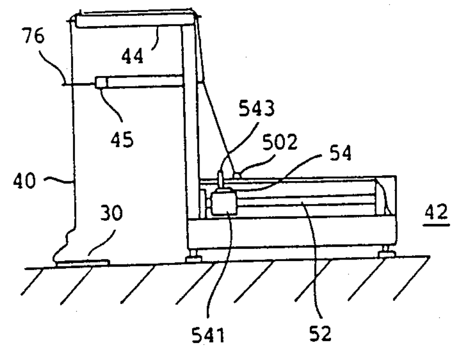
FIG. 7 shows an elevational view for use in describing the drop tester which is put into the state illustrated in FIG. 6.

Referring to FIGS. 6 and 7, the controller 60 delivers a first control signal to the additional cylinder 542 to project the cylinder pin 543 upwards of FIG. 5. Consequently, the cylinder pin 443 becomes higher than the string 40 tied to the support post 502 with the cylinder block 541 kept unmoved, as illustrated in FIGS. 6 and 7.

Figure 8:
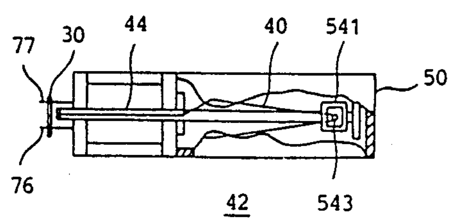
FIG. 8 shows a plan view for use in describing a subsequent state of the drop tester which follows the state illustrated in FIGS. 6 and 7.
Figure 9:
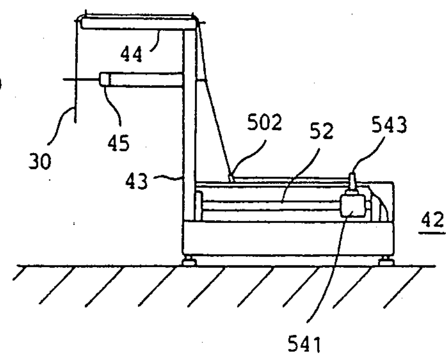
FIG. 9 shows an elevational view for use in describing the subsequent state of the drop tester like in FIG. 8.

Referring to FIGS. 8 and 9, the controller 60 supplies a second control signal to the cylinder block 541 to move the same backwards of FIG. 3, namely, rightwards of FIGS. 8 and 9. During such a rightward movement of the cylinder block 541, the cylinder pin 543 remains at a projected state and therefore hooks the string 40. Accordingly, the cylinder pin 543 pulls the string 40 right wars of FIGS. 8 and 9. As a result, the string 40 is approximately doubled up while the compact disk 30 is vertically hoisted to the predetermined height h. Accordingly, the predetermined distance may be shorter than the predetermined height h. This structure makes the drop tester compact. When the compact disk 30 is brought into contact with the first and the second detection needles 76 and 77, the detection signal is sent from the first and the second detection needles 76 and 77 to the controller 60.

Supplied with the detection signal, the controller 60 supplies a third control signal to the cylinder block 541 to stop the rightward movement of the cylinder block 541. On the other hand, the detection signal is counted up by the control circuit to be visually displayed on the display unit 61. Thus, a count or number of the repetitions is displayed on the display unit 61 each time when the detection signal is produced from the detecting member. When the cylinder block 541 is stopped in response to the detection signal, the cylinder block 541 does not reach the first limit switch 56 yet. This shows that the predetermined distance determined for the cylinder block 541 is longer than a half of the predetermined height h.

Figure 10:
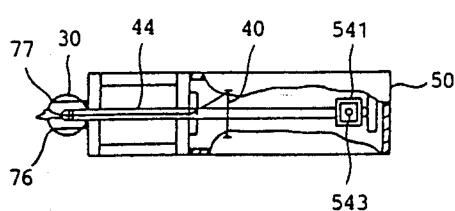
FIG. 10 shows a plan view for use in describing a next state of the drop tester which follows the subsequent state illustrated in FIGS. 8 and 9.
Figure 11:
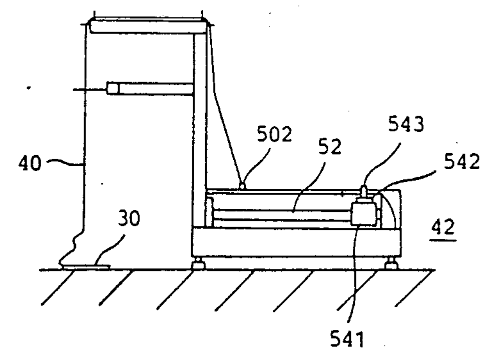
FIG. 11 shows an elevational view for use in describing the next state of the drop tester like in FIG. 10.

Referring to FIGS. 10 and 11, the controller 60 delivers a fourth control signal to the additional cylinder 542 to retract the cylinder pin 543 downwards of FIG. 11. This means that the string 40 is released from the cylinder pin 543 to be pulled leftwards by the compact disk 30 and the weight 72 downwards of FIG. 11. As a result, the compact disk 30 is freely dropped from the predetermined height h and collides with the floor, as shown in FIGS. 10 and 11, to be subjected to a mechanical shock.

Subsequently, the moving unit 54 is returned back to the leftmost position illustrated in Figs. 4 and 5 under control of the controller 60, with the cylinder pin 543 retracted downwards.

Thereafter, similar operation is repeated again and again until no detection signal is produced from the first and the second detection needles 76 and 77 to the controller 60. No production of the detection signal means that the compact disk 30 is not brought into contact with the first and the second detection needles 76 and 77 as a result of breakage of the compact disk 30. In this case, the moving unit 54 is moved to the first limit switch 56 when the compact disk 30 is not brought into contact with the first and the second detection needles 76 and 77. As a result, the first limit switch 56 is closed to produce an electric signal which is representative of completion of the drop test and which may be called a test completion signal.

Responsive to the test completion signal, the controller 60 may visually or audibly indicate completion of the drop test with the repetitions displayed on the display unit 61.

With this structure, it is possible to automatically and repeatedly carry out drop tests a great number of times once the drop tester is set into an operable state with the compact disk 30 tied to the string 40. In addition, repetitions of the drop tests can be automatically displayed on the display unit 61. Accordingly, the illustrated drop tester can save a lot of time and labor necessary for the drop tests. Moreover, it is also possible to avoid a miscount of the repetitions and to therefore accurately calculate the repetitions.

In the illustrated drop tester, the article, such as the compact disk 30, is always dropped from the predetermined height h kept unchanged. In other words, the drop tests are always carried out under the same conditions. This enables an accurate measurement of durability of the article. Attachment of the weight 72 to the string 40 serves to establish substantial free fall of the article because it is possible to avoid any influence of friction between the guide rings 66 to 70 and the string 40. The string 40 may be a fishing line which is very cheap and durable Such a fishing line is helpful to remarkably reduce a frictional resistance.

Figure 12:
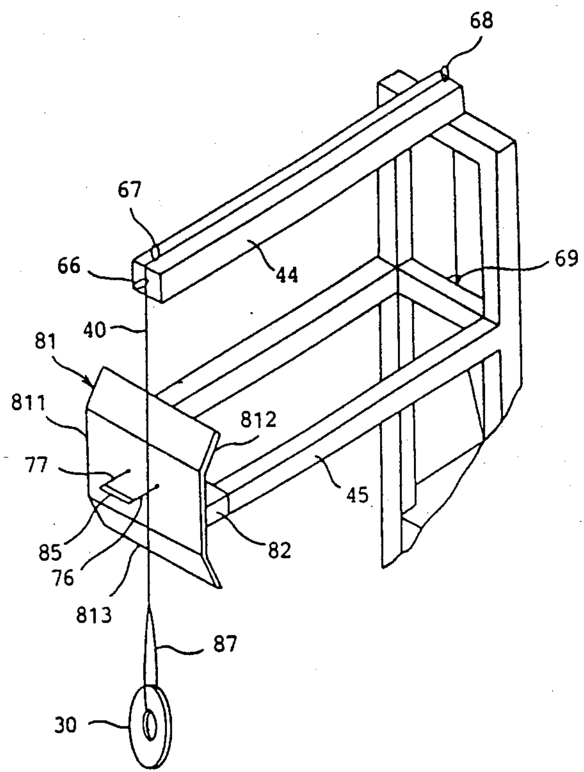
FIG. 12 is a partial perspective view of a drop tester according to a second embodiment of this invention.
Figure 13:
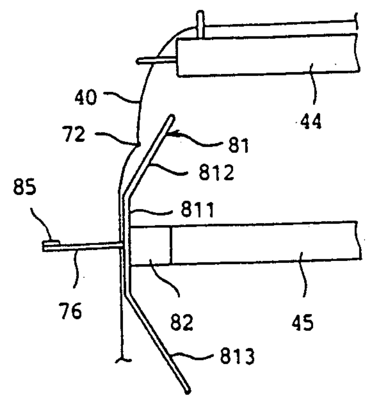
FIG. 13 is a partial elevational view of the drop tester illustrated in FIG. 12.

Referring to FIGS. 12 and 13, a drop tester according to a second embodiment of this invention is similar in structure and operation to that illustrated in FIGS. 3 through 11 except that a detection member is somewhat changed from that illustrated in FIG. 3. In FIGS. 12 and 13, the detection member is mounted on a disk guide plate 81 attached to the front bar (depicted at 82 in FIGS. 12 and 13) of the support frame 45. The illustrated detection member comprises first and second detection needles 76 and 77 like in FIG. 3 and a bridge bar 85 connected to the first and the second detection needles 76 and 77 at both ends of the needles. In the example being illustrated, the bridge bar 85 is formed by a thin steel plate having elasticity and has a thickness of, for example, 0.05 mm. Alternatively, the bridge bar 85 may be formed either by any other elastic material or by a nonelastic material. Furthermore, the bridge bar 85 may be formed by a fishing line.

At any rate, the bridge bar 85 may be elastically bent to some extent so that micro switches connected to the first and the second detection needle 76 and 77 are turned on each time when the compact disk 30 is brought into contact wit the first and the second detection needles 76 and 77. Preferably, the bridge bar 85 has elasticity or rigidity so that the compact disk 30 is not fixedly held between the bridge bar 85 and the disk guide plate 81 even when the compact disk 30 is interposed between the bridge bar 85 and the disk guide plate 81. The compact disk 30 is vertically suspended through a space surrounded by the first and the second detection needles 76 and 77 and the bridge bar 85, as illustrated in FIG. 12. With this structure, the compact disk 30 is always placed within the spacing defined by the first and the second detection needles 76 and 77 and the bridge bar 85 and is never swung outside of the spacing due to the bridge bar 85. In FIG. 12, the string 40 is extended through a center opening of the compact disk 30 and is looped at the first end of the string 40. Thus, the string 40 has a loop shaped portion 87 which suspends the compact disk 30. Such suspension or support of the compact disk 30 by the loop shaped portion 87 enables rotation of the compact disk 30 when a center of gravity of the compact disk 30 is changed due to partial breakage of the compact disk 30. The rotation of the compact disk 30 provides a secure contact of the compact disk 30 with the first and the second detection needles 76 and 77.

In FIGS. 12 and 13, the disk guide plate 81 has a center region 811 attached to the front bar of the support frame 45 and a pair of peripheral or inclined regions 812 and 813 contiguous to the center region 811. The peripheral regions 812 and 813 are inclined backwards relative to the string 40 at an acute angle. In any event, the disk guide plate 81 serves to preferably guide the compact disk 30 by forcibly directing each flat surface of the compact disk 30 towards the center region 811 in parallel when the compact disk 30 is hoisted to the disk guide plate 81. Therefore, the compact disk 30 perpendicularly intersects with the first and the second detection needles 76 and 77 by virtue of the disk guide plate 81 as long as the compact disk 30 is not completely broken. This shows that the compact disk 30 is reliably brought into contact with the first and the second detection needles 76 and 77 in comparison with FIG. 3. In addition, the inclined region 812 of the disk guide plate 81 serves to favorably guide the weight 72 and to allow the weight 72 to pass through the detection member without any stoppage.

Figure 14:
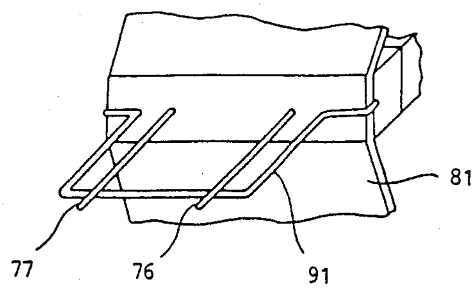
FIG. 14 is a partial perspective view of a drop tester according to a third embodiment of this invention.

Referring to FIG. 14, a detection member is for use in a drop tester according to a third embodiment of this invention and comprises, in addition to the first and the second detection needles 76 and 77, a partition member 91 of a figure of "U" shape which is located slightly under the first and the second detection needles 76 and 77 along an outer periphery of the first and the second detection needles 76 and 77 and which is fixed to the disk guide plate 81. More specifically, the partition member 91 ha end portions fixed to the center region of the disk guide plate 81, a pair of parallel portions substantially parallel to the first and the second detection needles 76 and 77, and portion which is contiguous to the parallel portions and which intersects the first and the second detection needles 76 and 77. In the illustrated partition member 91, the first and the second detection needles 76 and 77 are protruded from the partition member 91 at ends of the first and the second detection needles 76 and 77, as shown in FIG. 14. Thus, a closed plane is defined or partitioned by the partition member 91 and the disk guide plate 81.

With this structure, the string 40 (not shown in this figure) passes through an internal space defined by the first and the second detection needles 76 and 77 and the partition member 91. As a result, a swingable range of the compact disk 30 is defined by the partition member 91 like in FIGS. 12 and 13.

While this invention has thus far been described in conjunction with a few embodiments thereof, it will readily be possible for those skilled in the art to put this invention into practice in various other manners. For example, the moving unit 54 may be driven by electromagnetic solenoids or the like. The controller 60 may be implemented by a microcomputer. The detection member may be of a noncontact type which uses infrared radiation or the like. The string 40 may be composed of a high molecular substance different from that of the fishing line or may be of a high molecular fiber. The article may be, for example, a glass disk, a plastic disk, a memory disk, or the like, although the compact disk 30 has been exemplified.

What is claimed is:

1. A drop tester for use in freely and repeatedly dropping an article from a predetermined height to test durability of said article until said article is destructed, said drop tester comprising:

a string member having a first end for supporting said article, a second end, and an intermediate portion between said first and said second ends;

guiding means for slidably guiding said string member to suspend said article;

driving means associated with said string member at said second end through said guiding means for repeatedly and automatically driving said string member within a predetermined range to elevate said article to said predetermined height with said article held at said first end and to thereafter freely drop said article from said predetermined height;

detecting means for detecting that said article is elevated to said predetermined height by said driving means to produce a detection signal each time when said article is elevated to said predetermined height and, otherwise, to stop producing said detection signal; and counting means coupled to said detecting means for successively counting said detection signal until said detection signal is stopped to produce a count signal representative of a result of the count; and display means coupled to said counting means for displaying said count signal.

2. A drop tester as claimed in claim 1, wherein said guiding means comprises:

a support post located at a predetermined position for fastening said second end of the string member;

a tower frame member standing upright and having a tower height higher than said predetermined height, said tower frame member being adjacent to said predetermined position, the intermediate portion of said string member being extended from said support post along said tower frame; and a horizontal guide member having a first preselected length and a first guide end fixed to said tower frame member, and a second guide end, said horizontal guide member being substantially horizontally extended from said tower frame to horizontally guide said string member, said string member dropping through said second guide end to suspend said article tied at said first end of the string member.

3. A drop tester as claimed in claim 2, wherein said detecting means comprises:

a support frame which has a second preselected length shorter than said first preselected length and which is juxtaposed with said horizontal guide member, said support frame being fixed to said tower frame member at said predetermined height; and a pair of detection needles attached to said support frame at said predetermined height with a space left therebetween so that said article is brought into contact with said detection needles at said predetermined height.

4. A drop tester as claimed in claim 3, wherein said detecting means further comprises:

a bridge bar connected between said detection needles.

5. A drop tester as claimed in claim 4, wherein said detecting means further comprises:

a disk guide plate having a center region attached to said support frame and a pair of peripheral regions contiguous to said center region on both sides of said center region, said peripheral regions being inclined relative to said center region towards said tower frame member.

6. A drop tester as claimed in claim 4, wherein said detecting means comprises:

a partition member attached to said support frame, said partition member having a pair of parallel portions substantially parallel to said detection needles and a portion contiguous to said parallel portions to intersect said detection needles.

7. A drop tester as claimed in claim 2, wherein said driving means comprises:

a cylinder member horizontally extended for defining said predetermined range; and a moving unit movable along said cylinder member for horizontally and reciprocally moving said string member within said predetermined range.

8. A drop tester as claimed in claim 7, wherein said driving means comprises:

a case having a slit defining said predetermined range to accommodate said cylinder member and said moving unit to define said predetermined position for said support post thereon.

* * * * *